(12) United States Patent
Patrick et al.

(10) Patent No.: US 7,905,822 B2
(45) Date of Patent: Mar. 15, 2011

(54) BRACHYTHERAPY METHOD AND APPLICATOR FOR TREATMENT OF METASTATIC LESIONS IN A LOAD BEARING REGION

(75) Inventors: Timothy J. Patrick, Alpharetta, GA (US); James B. Stubbs, Alpharetta, GA (US)

(73) Assignee: Cytyc Corporation, Marboro, MA (US)

( * ) Notice: Subject to any disclaimer, the term of this patent is extended or adjusted under 35 U.S.C. 154(b) by 582 days.

(21) Appl. No.: 10/995,087

(22) Filed: Nov. 22, 2004

(65) Prior Publication Data

US 2005/0113629 A1 May 26, 2005

Related U.S. Application Data

(60) Provisional application No. 60/523,550, filed on Nov. 20, 2003.

(51) Int. Cl.
*A61N 5/00* (2006.01)
(52) U.S. Cl. .......................................................... 600/8
(58) Field of Classification Search ................. 600/1–8; 623/1.34, 32
See application file for complete search history.

(56) References Cited

U.S. PATENT DOCUMENTS

| | | | |
|---|---|---|---|
| 3,324,847 A | 6/1967 | Zoumboulis | |
| 3,872,856 A | 3/1975 | Clayton | |
| 4,417,576 A | 11/1983 | Baran | |
| 4,706,652 A | 11/1987 | Horowitz | |
| 4,754,745 A | 7/1988 | Horowitz | |
| 4,763,642 A | 8/1988 | Horowitz | |
| 4,821,725 A | 4/1989 | Azam et al. | |
| 4,867,741 A | 9/1989 | Portnoy | |
| 5,015,247 A | 5/1991 | Michelson | |
| 5,084,001 A | 1/1992 | Van't Hooft et al. | |
| 5,084,015 A | 1/1992 | Moriuchi | |
| 5,106,360 A | 4/1992 | Ishiwara et al. | |
| 5,112,303 A | 5/1992 | Pudenz et al. | |
| 5,152,747 A | 10/1992 | Olivier | |
| 5,236,410 A | 8/1993 | Granov et al. | |
| 5,422,926 A | 6/1995 | Smith et al. | |

(Continued)

FOREIGN PATENT DOCUMENTS

DE 41 09 205 A1 9/1992

(Continued)

OTHER PUBLICATIONS

Ravinder, Nath, Ph.D. et al., Development of an [241] Am Applicator for Intracavitary Irradiation of Gynecologic Cancers, *I.J. Radiation Oncology, Biology, Physics*, May 1988, vol. 14, pp. 969-978.

(Continued)

*Primary Examiner* — Charles A Marmor, II
*Assistant Examiner* — Christine D Hopkins
(74) *Attorney, Agent, or Firm* — Lindsay McGuinness

(57) ABSTRACT

A brachytherapy applicator for treatment of metastic lesions in a load bearing region is provided. The applicator comprises an elongate tube body having a proximal and a distal end and defining an open internal area. A fixation element located on an outer portion of the tube allows the applicator to be fixed in position in relation to a target region while delivering a dose of therapeutic radiation. The fixation element can fix the applicator to tissue and/or a stabilization element implanted within a patient. A source of radiation positioned within the elongate body, before, during, or after implantation of the applicator, provides the therapeutic radiation.

24 Claims, 10 Drawing Sheets

U.S. PATENT DOCUMENTS

| | | | |
|---|---|---|---|
| 5,484,384 A | 1/1996 | Fearnot | |
| 5,562,594 A | 10/1996 | Weeks | |
| 5,566,221 A | 10/1996 | Smith et al. | |
| 5,720,717 A | 2/1998 | D'Andrea | |
| 5,724,400 A | 3/1998 | Swerdloff et al. | |
| 5,741,253 A | 4/1998 | Michelson | |
| 5,800,333 A | 9/1998 | Liprie | |
| 5,803,895 A | 9/1998 | Kronholz et al. | |
| 5,851,173 A | 12/1998 | Dugan | |
| 5,851,182 A | 12/1998 | Sahadevan | |
| 5,863,284 A | 1/1999 | Klein | |
| 6,036,631 A | 3/2000 | McGrath et al. | |
| 6,120,540 A | 9/2000 | Apple et al. | |
| 6,175,760 B1 * | 1/2001 | Baskin et al. | 600/436 |
| 6,251,060 B1 | 6/2001 | Hooft et al. | |
| 6,261,586 B1 | 7/2001 | McKay | |
| 6,264,599 B1 | 7/2001 | Slater et al. | |
| 6,413,204 B1 | 7/2002 | Winkler et al. | |
| 6,494,883 B1 | 12/2002 | Ferree | |
| 6,558,386 B1 | 5/2003 | Cragg | |
| 6,645,135 B1 | 11/2003 | Bhat | |
| 6,665,555 B2 | 12/2003 | Henderson et al. | |
| 6,666,811 B1 * | 12/2003 | Good | 600/8 |
| 6,695,760 B1 | 2/2004 | Winkler et al. | |
| 6,709,379 B1 | 3/2004 | Brandau et al. | |
| 6,723,128 B2 | 4/2004 | Uk | |
| 6,740,093 B2 | 5/2004 | Hochschuler et al. | |
| 6,749,555 B1 | 6/2004 | Winkler et al. | |
| 6,790,233 B2 | 9/2004 | Brodke et al. | |
| 7,029,431 B2 * | 4/2006 | Apple et al. | 600/3 |
| 2004/0167625 A1 | 8/2004 | Beyar et al. | |

FOREIGN PATENT DOCUMENTS

| | | |
|---|---|---|
| EP | 0 340 881 | 10/1992 |
| EP | 0 867 200 | 9/1998 |
| WO | WO 92/10932 | 7/1992 |
| WO | WO 93/09724 | 5/1993 |
| WO | WO 97/19723 | 6/1997 |
| WO | WO 99/11325 | 3/1999 |
| WO | WO 99/33515 | 7/1999 |
| WO | WO 99/42163 | 8/1999 |
| WO | WO-00/09212 | 2/2000 |
| WO | WO 01/43826 A1 | 6/2001 |
| WO | WO 01/68005 A2 | 9/2001 |
| WO | WO-02/40092 | 5/2002 |
| WO | WO-02/100480 | 12/2002 |

OTHER PUBLICATIONS

Ashpole, R.D. et al., "A New Technique of Brachytherapy for Malignant Gliomas with Caesium-137: A New Method Utilizing a Remote Afterloading System," *Clinical Oncology*, vol. 2, 333-7 (1990).

* cited by examiner

BRACHYTHERAPY METHOD AND APPLICATOR FOR TREATMENT OF METASTATIC LESIONS IN A LOAD BEARING REGION

CROSS-REFERENCE TO RELATED APPLICATIONS

This U.S. patent application claims priority to U.S. Provisional Application Ser. No. 60/523,550, entitled, "Brachytherapy Method and Applicator for Treatment of Metastatic Lesions in a Load Bearing Region," filed Nov. 20, 2003, which is incorporated herein by reference in its entirety.

FIELD OF THE INVENTION

The invention relates generally to methods and applicators for use in treating proliferative tissue disorders, and more particularly to an apparatus for the treatment of such disorders in a load-bearing region of a patient by the application of radiation.

BACKGROUND OF THE INVENTION

Malignant tumors are often treated by surgical resection of the tumor to remove as much of the tumor as possible. Infiltration of the tumor cells into normal tissue surrounding the tumor, however, can limit the therapeutic value of surgical resection because the infiltration can be difficult or impossible to treat surgically. Radiation therapy can be used to supplement surgical resection by targeting the residual malignant cells after resection, with the goal of sterilizing them, reducing the rate of recurrence or delaying the time to recurrence. Radiation therapy can be administered through one of several methods, or a combination of methods, including permanent or temporary interstitial brachytherapy, and external-beam radiation.

Brachytherapy refers to radiation therapy delivered by a spatially confined source of therapeutic rays inserted into the body at or near a tumor or other proliferative tissue disease site. For example, brachytherapy can be performed by implanting radiation sources directly into the tissue to be treated. Brachytherapy is most appropriate where 1) malignant tumor regrowth occurs locally, within 2 or 3 cm of the original boundary of the primary tumor site; 2) radiation therapy is a proven treatment for controlling the growth of the malignant tumor; and 3) there is a radiation dose-response relationship for the malignant tumor, but the dose that can be given safely with conventional external beam radiotherapy is limited by the tolerance or normal tissue. In brachytherapy, radiation doses are highest in close proximity to the radiotherapeutic source, providing a high tumor dose while sparing surrounding normal tissue.

Prior art brachytherapy devices have provided a number of advancements in the delivery of radiation to target tissue. For example, Winkler U.S. Pat. No. 6,413,204 describes a brachytherapy method and apparatus for treating tissue surrounding a surgically excised tumor with radioactive emissions to kill cancer cells that may be present in the tissue surrounding the excised tumor. The radiation is delivered in a predetermined dose range defined as being between a minimum prescribed absorbed dose for delivering therapeutic effects to tissue that may include cancer cells, and a maximum prescribed absorbed dose above which healthy tissue necrosis may result. The resulting treatment helps to prevent overexposure to tissue at or near the brachytherapy device, while still delivering the minimum prescribed dose at the maximum prescribed distance from the device.

Brachytherapy is useful for treating malignant brain and breast tumors, among others. However, malignant tumors in other regions of the body, such as load bearing regions, can provide particular challenges. For example, malignant tumors related to the spinal column often require surgical resection followed by stabilization to promote proper healing. Surgical stabilization can be performed in an open procedure where a surgeon places the patient's bone, bones, or other load bearing structure in a desired position that remains stable while the patient is located in the operating room. Additionally, stabilization devices such as cages used in spinal fusion procedures can be implanted to stabilize the load-bearing region. Still further, the stabilization could be achieved using expandable bodies such as those described in U.S. Pat. No. 6,248,110 entitled "Systems and Methods for Treating Fractured or Diseased Bone Using Expandable Bodies," issued on Jun. 19, 2001 to Reiley et al., which patent is hereby incorporated by reference.

Treatments utilizing such expandable bodies for stabilization include insertion of the expandable body (e.g., a balloon) to compress cancellous bone and provide an interior cavity. For example, the expandable body can be inflated inside a damaged or weakened vertebral body. The interior cavity then receives a filling material, such as a cement-like material, which hardens and provides renewed structural support. Unfortunately, such procedures limit the access of traditional balloon catheter devices used to deliver brachytherapy radiation to soft tissue.

As such, while advancements have improved the treatment of proliferative tissue diseases, some challenges remain. In particular, delivering brachytherapy radiation to the load bearing aspects of a patient's body (e.g., tissue of or adjacent to vertebral bodies) in combination with a stabilization procedure has proven difficult.

SUMMARY OF THE INVENTION

Disclosed herein is a brachytherapy applicator and methods of treating metastases within a load bearing portion of a patient's body. The brachytherapy applicator is adapted for delivering therapeutic radiation to a target area that includes bony tissue, particularly in association with stabilization treatments. Fixation elements on the applicator can secure the device in position relative to target tissue and provide a stable platform for delivering radiation.

In one aspect, the brachytherapy applicator comprises an elongate tube body having a proximal end, a distal end, and an open internal area. One or more radiation sources provided within the internal area can deliver a therapeutic dose. In addition, a fixation element can be located on an outer portion of the tube. In one exemplary embodiment, the fixation element is a bone attachment element including a bone screw thread provided on a closed distal end of the tube body.

In another embodiment, the outer surface of the tube includes an attachment element adapted to fix the applicator within a filling material after the filling material hardens. For example, such attachment elements include one or more barbs or a depression in the tube body that can receive filling material prior to hardening.

The proximal end of the applicator can include an opening to the internal area and a resealable end cap covering the opening. In one aspect, the end cap is detachable. In addition, the proximal end of the applicator can mate with a catheter for delivery (or removal) of a radiation source to (from) the open internal area.

In another aspect of the applicator, the applicator body includes a bifurcated arm that is positionable at an angle with respect to the hollow tube. The bifurcated arm can include a radiation source configured to provide a therapeutic radiation dose. In one embodiment, the bifurcated arm allows the applicator to deliver an asymmetric dose of radiation to an irregularly shaped vertebral body.

A method for treating proliferative tissue disorders in a load-bearing region is also disclosed. In one embodiment, the method includes providing an applicator comprising an elongate tube body having a proximal and a distal end, where the tube body defines an open internal area. Additional steps include implanting the applicator, positioning a radiation source within the internal area, and providing a therapeutic dose of radiation.

In one embodiment, the step of positioning the radiation source occurs before implanting the applicator. In another embodiment, the step of positioning a radiation source occurs after the step of implanting. For example, a catheter can be mated to the applicator after implantation and a radiation source can be delivered through the catheter.

In another embodiment, a brachytherapy applicator and method of use is disclosed. The brachytherapy applicator can be used with radiation sources that are permanently embedded in the applicator, temporarily placed in the applicator for several days (low dose rate, LDR, brachytherapy) or only several minutes (high dose rate, HDR, brachytherapy). The brachytherapy applicator can be adapted for any sort of HDR brachytherapy, such as, for example, urethral strictures, spinal lesions, interstitial (e.g., breast, soft tissue, sarcomas, etc.), endobronchial, and other intracavitary brachytherapies. The applicator includes a radiation containing body defining an internal volume and one or more radiation sources provided within the internal volume. The radiation source is a photon source, and in one aspect, provides less than about 100 keV. In another aspect, the radiation source provides energy in the range of about 25 keV to 80 keV.

BRIEF DESCRIPTION OF THE DRAWINGS

The invention can be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

In general, disclosed herein are methods and devices for the delivery of radiation therapy to load-bearing portions of a patient's body. In one aspect, a brachytherapy applicator for delivering brachytherapy radiation to a load-bearing region, particularly a load bearing region stabilized with a filling material, is disclosed. The applicator includes a rigid body adapted for implantation into bone and/or a filling material. Once implanted, a therapeutic dose of radiation can be delivered to the residual tumor margin.

Figure 1:
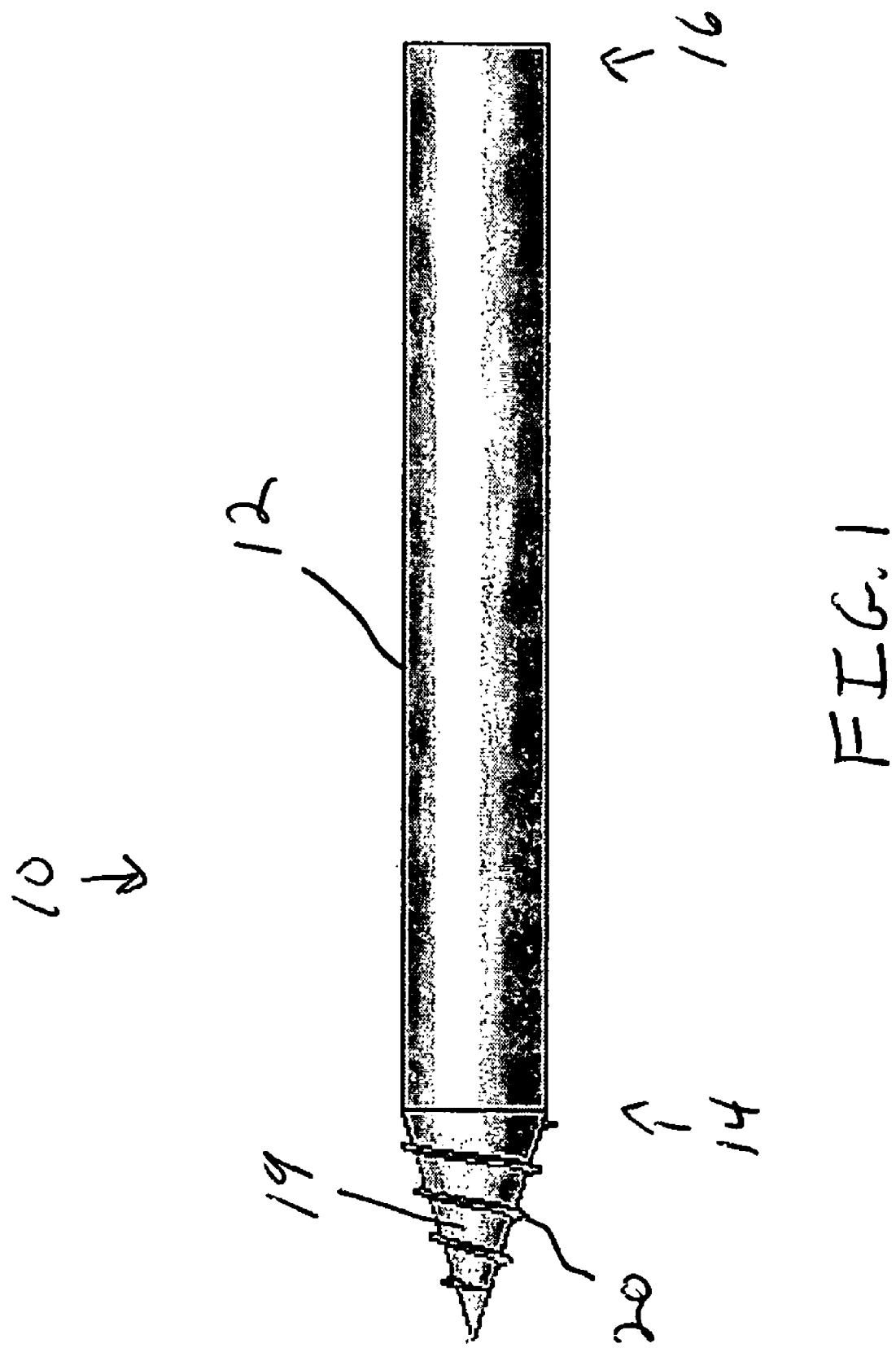
FIG. 1 is a side view of one embodiment of the brachytherapy applicator designed for delivering therapeutic radiation to a load bearing region.
Figure 2:
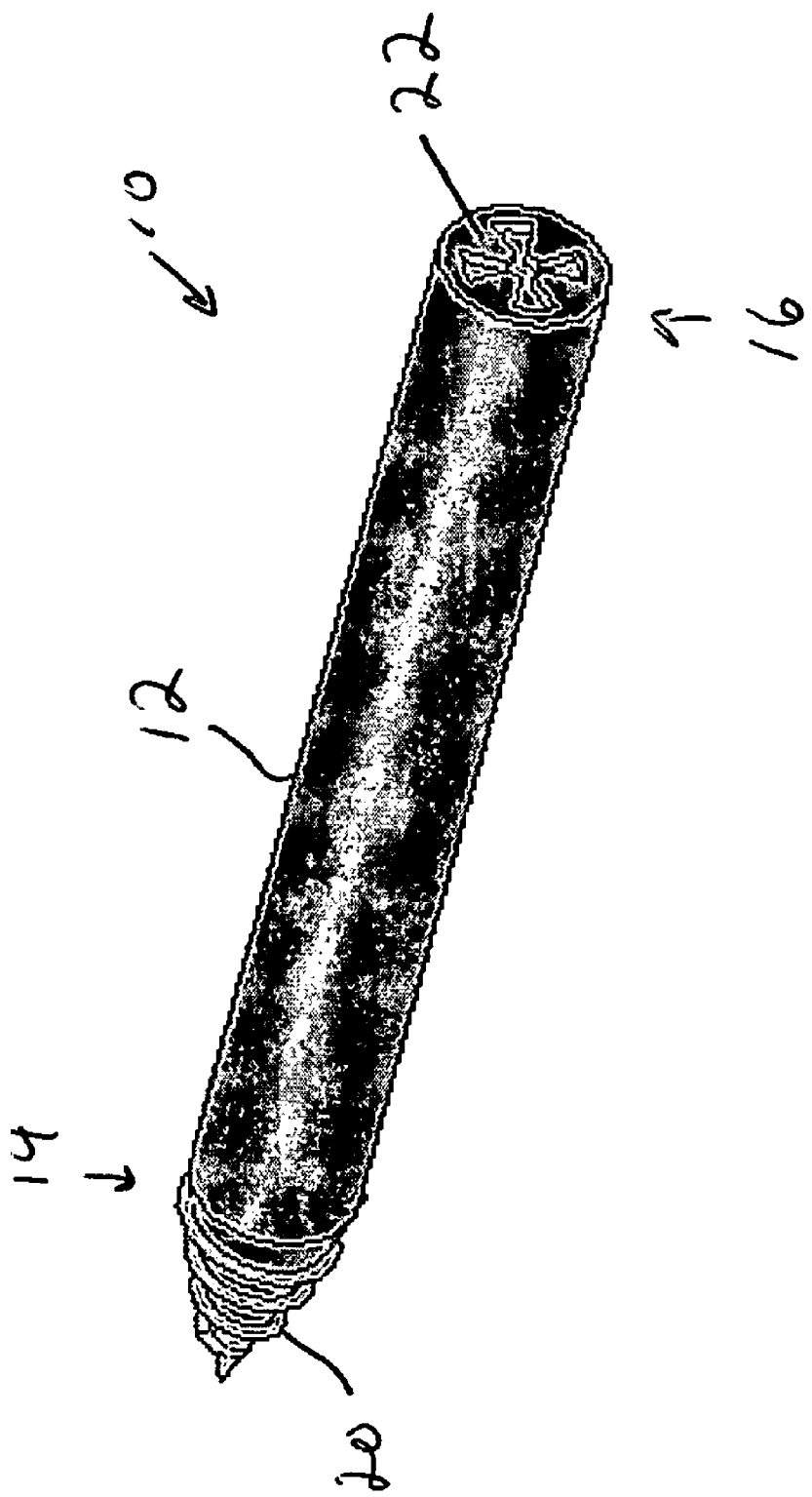
FIG. 2 is a perspective view of the applicator of FIG. 1.

One exemplary brachytherapy applicator is illustrated in FIGS. 1 and 2. As shown, applicator 10 can include an elongate body 12 having a proximal end 16 and a distal end 14. In one aspect, distal end 14 can be adapted for insertion into tissue and/or filling material and proximal end 16 can open to an internal hollow region 17. Inner hollow region 17 (FIGS. 5 and 6) can hold a therapeutic radiation source 18 during treatment.

Distal end 14 can provide a closed tip region 19 having mechanical features 20. In one aspect, mechanical features 20 allow applicator 10 to be secured within or adjacent to a body structure (e.g., a vertebral body). For example mechanical feature 20 might have a configuration similar to a bone screw or a threaded, sharp distal point like a wood screw. This allows direct fixation via mechanical means into a bony structure. Other mechanical fixation components may be like a mechanical claw that grips a tissue surface in contact with the device. Mechanical features 20 also allow direct fixation into a hardened filling material.

In another aspect, applicator 10 is implanted into an unhardened filling material and mechanical features 20 provide fixation once the filling material hardens around the mechanical features. For example, if applicator 10 is placed within a vertebral body along with a cement-like material, the mechanical features can hold the applicator in a desired location once the cement-like material hardens.

Figure 3:
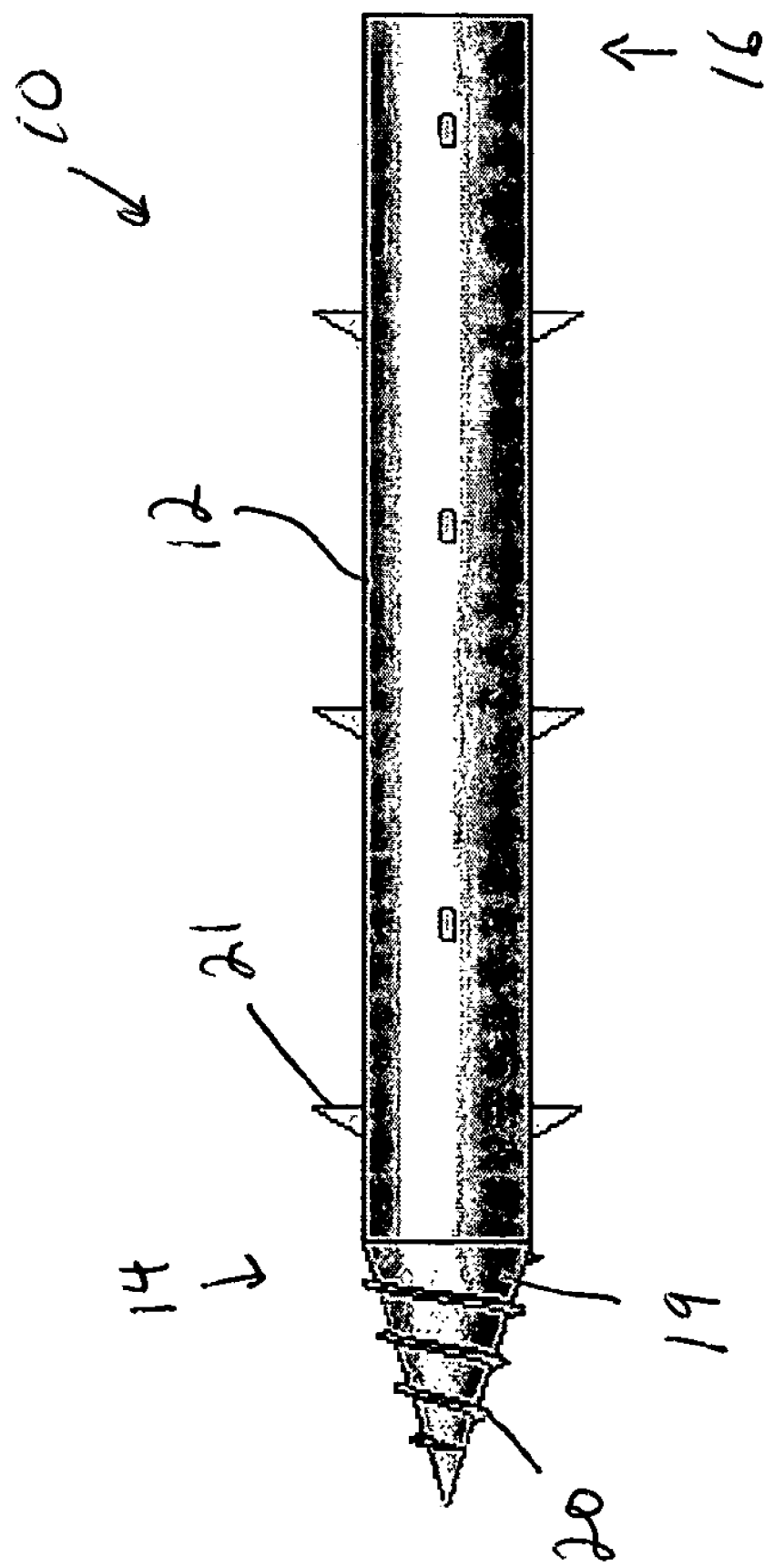
FIG. 3 is a side view of another embodiment of the brachytherapy applicator.
Figure 4:
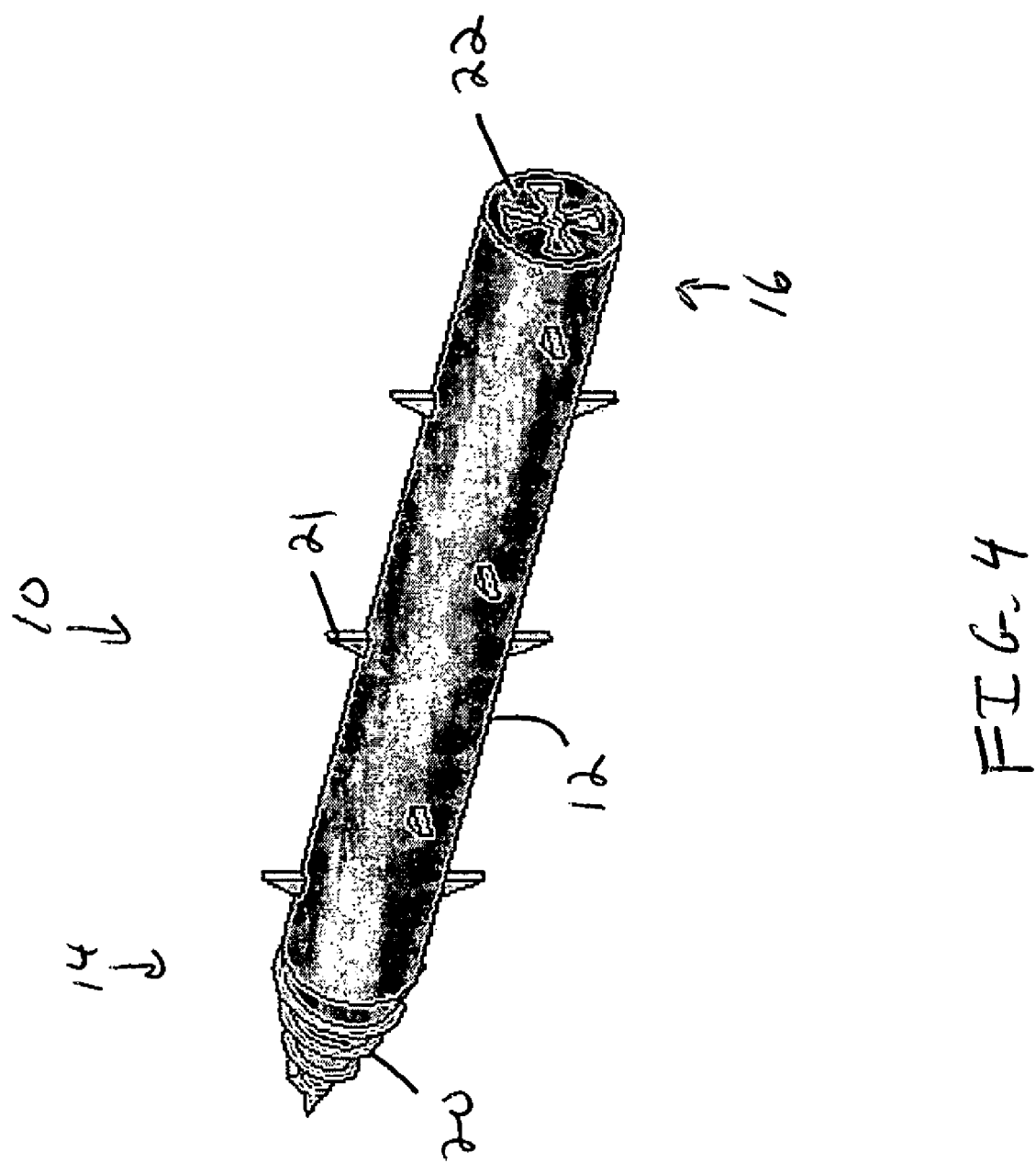
FIG. 4 is a perspective view of the applicator of FIG. 3.

As an alternative to mechanical features 20, or in addition, the outer surface of body 12 can include securement features 21 useful for securing applicator 10 within the interior of the bony structure filled with an unhardened cement-like substance (e.g., PMMA, poly-methylmethacrylate). For example, body 12 can have one or more (e.g., a series) of barbs or blades as shown in FIGS. 3 and 4. When the applicator is implanted in an unhardened cement-like substance, the securement features become permanently fixed after hardening. Other protruding features can likewise act as securement features such as ridges or knobs extending from the outer surface of body 12

In another embodiment, applicator 10 can include other alternative features designed to fix the applicator within filling material after hardening. For example, the applicator body can include depressions (not shown) into which filling material can flow prior to hardening. As another example, the applicator body 12 can have an irregular shape such that after filling material flows around the irregularly shaped body and hardens, body 12 can not be withdrawn.

In yet another embodiment, securement feature 21 can be retractable such that applicator could be with drawn after implantation without destroying the hardened filling material. In one example, retractable fins or blades can facilitate releasable securement of the applicator.

Securing the applicator in place, regardless of the features used, fixes the applicator relative to the target region. As a result, a therapeutic dose can be effectively delivered to the residual tumor margin within the target tissue and the exposure of healthy tissue can be minimized.

In one embodiment, the therapeutic radiation source is loaded into the applicator prior to or after implantation. For example, the proximal end 16 of the body 12 can provide a path for ingress and egress of a radiation source from the interior of body 12. An end piece 22, as shown in FIGS. 2 and 4, can provide a resealable opening. One of ordinary skill in the art will appreciate that end piece 22 can mate with body 12 in a variety of ways, including by way of non-limiting example, threaded, snap fit, interference fit, and slot and groove. In addition, end piece 22 could in one embodiment be detachable from body 12.

End piece 22 can also provide a surface for mating with a tool. As shown in FIGS. 2 and 4, end piece 22 is cross slotted to receive a driver tool. In one embodiment, applicator 10 can attach to a driver tool for insertion into the bony structure during an open or percutaneous procedure. One skilled in the art will appreciate that the mating feature can have a variety of shapes and be formed in or on end piece 22.

In another aspect of the detachable end piece 22, the end piece is magnetic. In use it can be held to the tip of a tool using magnetic attraction between the tool and the end piece. The tool can then be used to position and mate the end piece to the applicator, as well as, to remove the end piece. Alternatively, the tool could be magnetic and the end piece attracted by the magnetic tool (e.g., a ferrous end piece).

The proximal end 16 of body 12 can include other features, such as feature for mating with a medical device. In one embodiment, the proximal end mates with a catheter for delivering a radiation source and includes surface feature adapted for receiving the end of a catheter. For example, the proximal end can include a barb (not shown) that assists with mating or suturing a catheter to the applicator.

Figure 5:
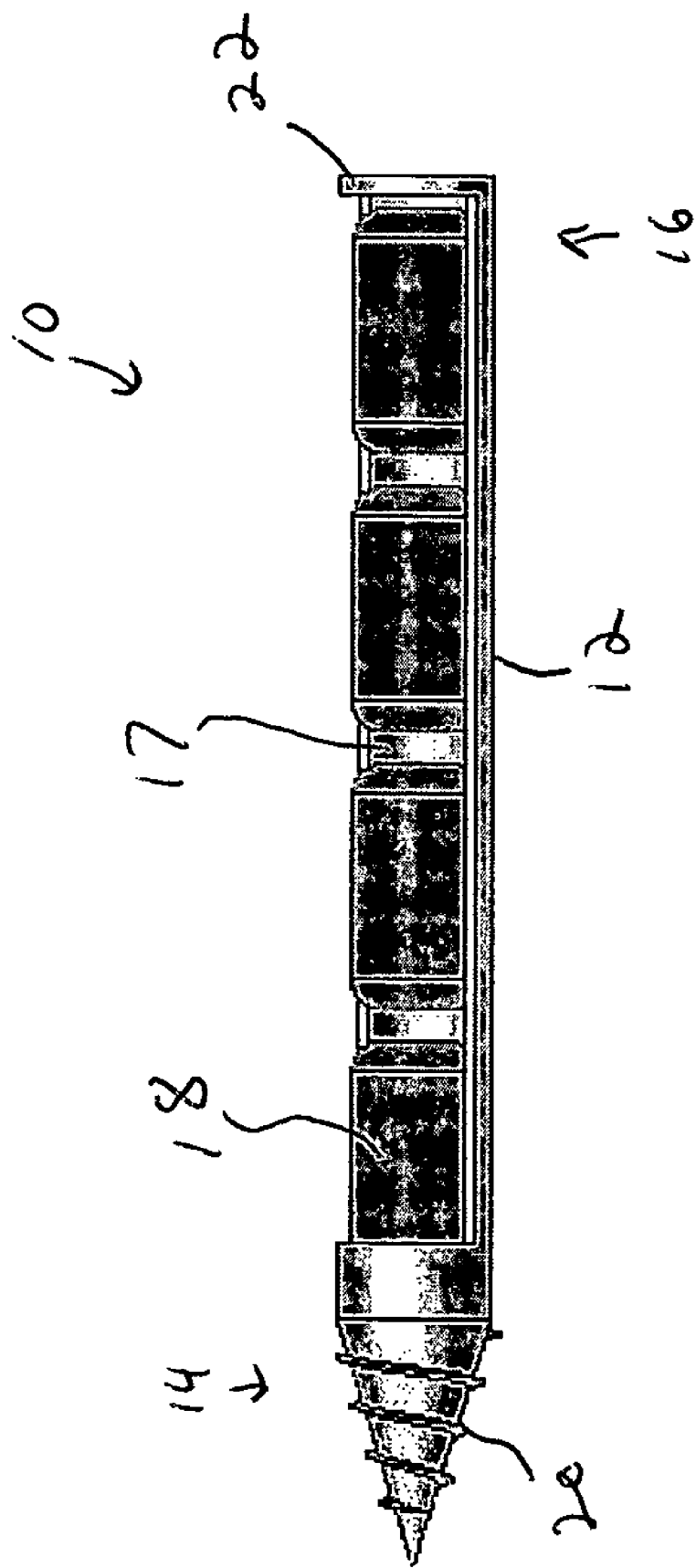
FIG. 5 is a sectional view of yet another embodiment of the brachytherapy applicator.
Figure 6:
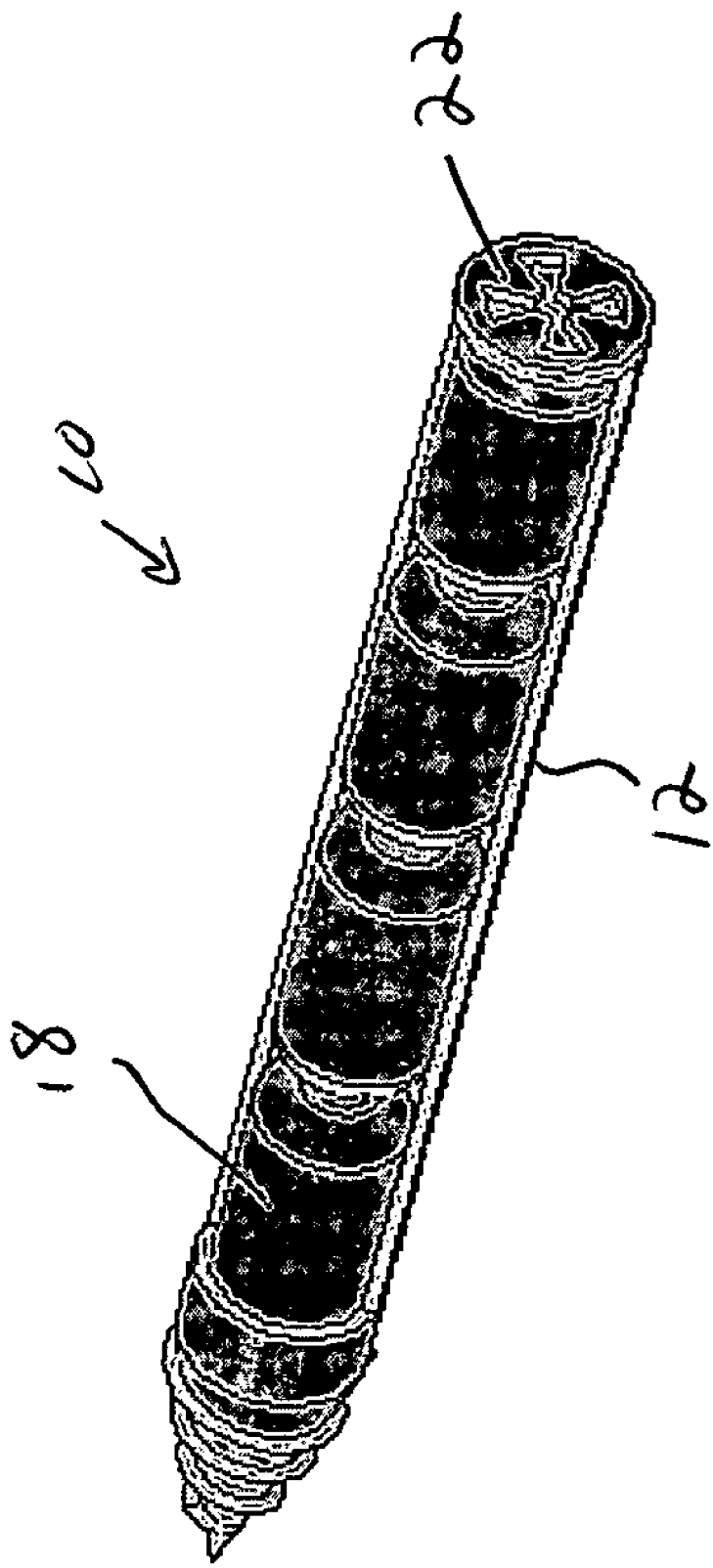
FIG. 6 is a perspective, sectional view of the applicator of FIG. 5.

Within the interior of body 12, a therapeutic radiation source can be positioned. For example, FIGS. 5 and 6 show a sectional view of applicator 10 with radiation source 18 positioned therein. The radiation source 18, in one embodiment, extends thought the length of hollow region 17. Source 18 may be provided as a single, long source of nearly the length of the inside of the tube (and smaller diameter than the inner tube diameter) or may be a series of smaller cylindrical or other shaped sources configured to provide the desired dose (i.e., dose shape and dose strength). Smaller radiation sources can be connected to each other by any means, including by way of non-limiting example, via welds or by enclosure in a metal strand or suture-like material. The train or series of sources may be of equal strength (in terms of emitted radiation), variable strength, or some of no activity, providing a means of varying the dose delivered along the length of the source.

In another embodiment, the radiation source occupies part of hollow region 17. For example, where the desired dose requires a lower volume of radiation source material than the interior volume of the hollow region, place holders can secure the radiation-emitting material within applicator 10. In addition, one skilled in the art will appreciate that hollow region 17 could also include a variety of other elements such as radiation shielding, directing, and/or sensing elements.

The radiation source system may provide a radially symmetric radiation dose profile with respect to the axial length of applicator body 12 or may provide an asymmetric radial dose profile. For a description of such dosing profiles, reference is made to U.S. Pat. No. 6,413,204, issued on Jul. 2, 2002 to Winkler et al., and entitled "Interstitial Brachytherapy Apparatus and Method for Treatment of Proliferative Tissue Diseases," which patent is incorporated herein by reference in its entirety. Asymmetric profiles could be accomplished using eccentric source positioning within the tube, angling or curving of the tube, and internal sources or partial shielding of the tubes and sources. Further examples of asymmetric dosing techniques can be found in U.S. Pat. No. 6,482,142, entitled "Asymmetric Radiation Dosing Apparatus and Method" and issued to Winkler et al. on Nov. 19, 2002, which patent is incorporated herein by reference in its entirety. The asymmetric dosing profile is useful to spare sensitive or normal tissues such as the spinal cord, small bowel, and/or intestine.

In one embodiment, the applicator can include an extended portion adapted for delivering a shaped radiation dose. For example, a bifurcation arm 30 is illustrated in FIGS. 7 through 10. The bifurcation arm can accommodate another set of one or more seeds positioned at an angle with respect to the axis L of body 12. This bifurcated arm 30 could articulate in that axis L of the body and an axis X of the bifurcated arm are parallel and in contact while being deployed into the bony structure and the arm could articulate into a subtended angle once in the desired position within the bony structure. The bifurcation arm could also be deployed as the applicator is inserted into a patient.

Figure 7:
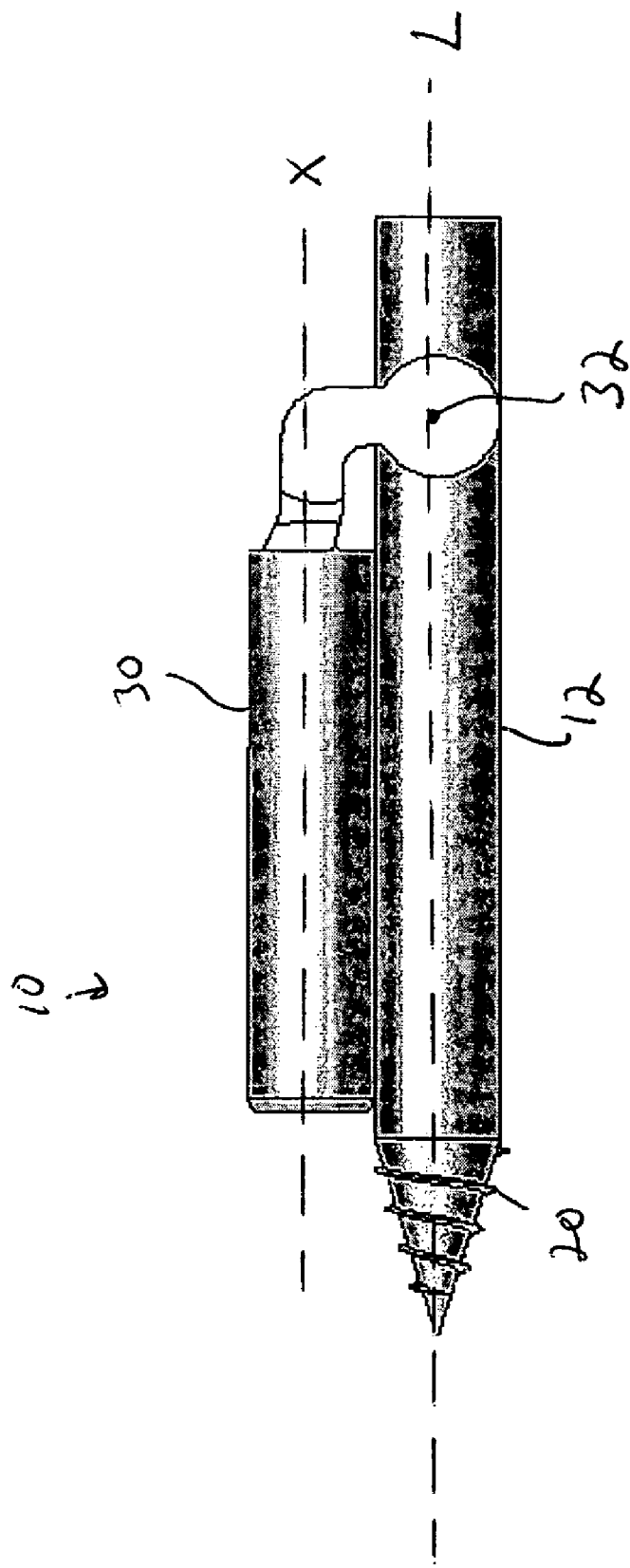
FIG. 7 is a side view of the brachytherapy applicator with a bifurcated arm.
Figure 8:
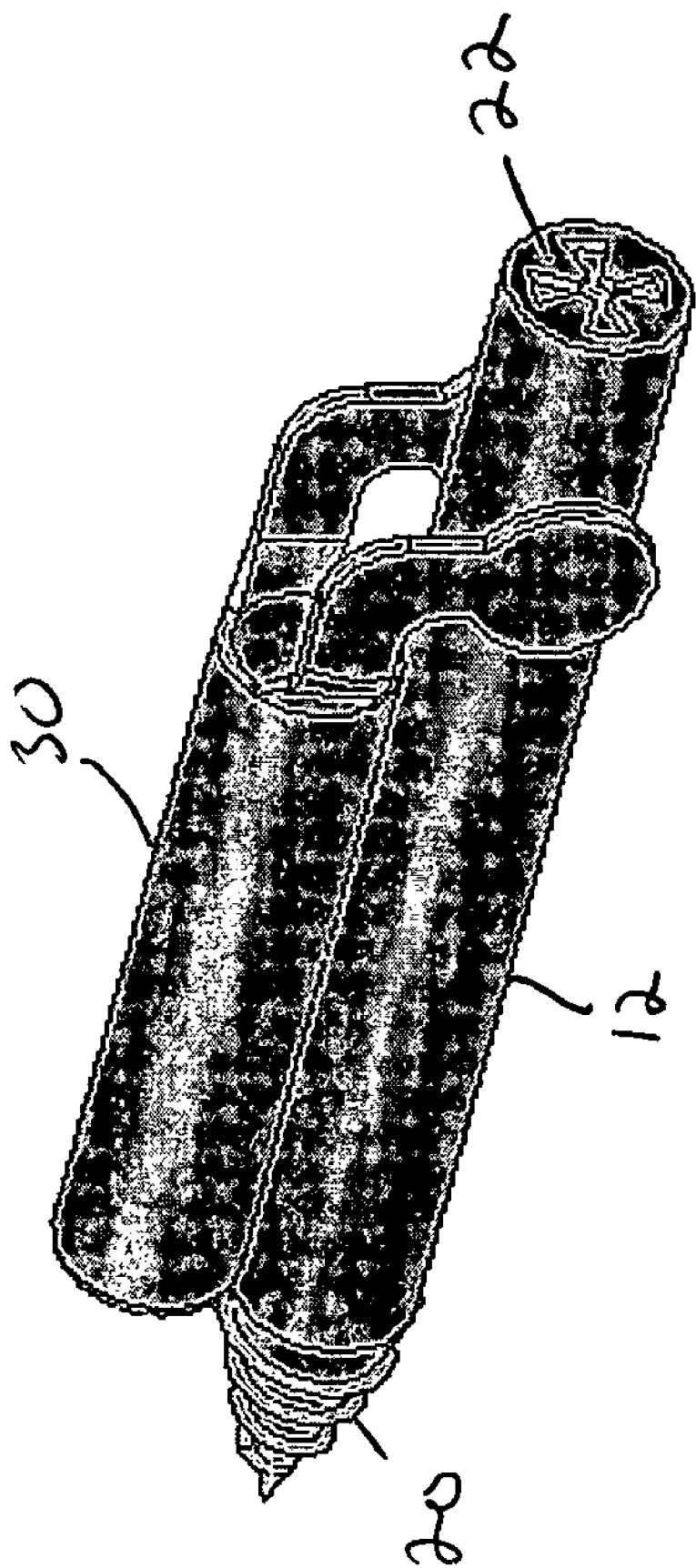
FIG. 8 is a perspective view of the applicator of FIG. 7.
Figure 9:
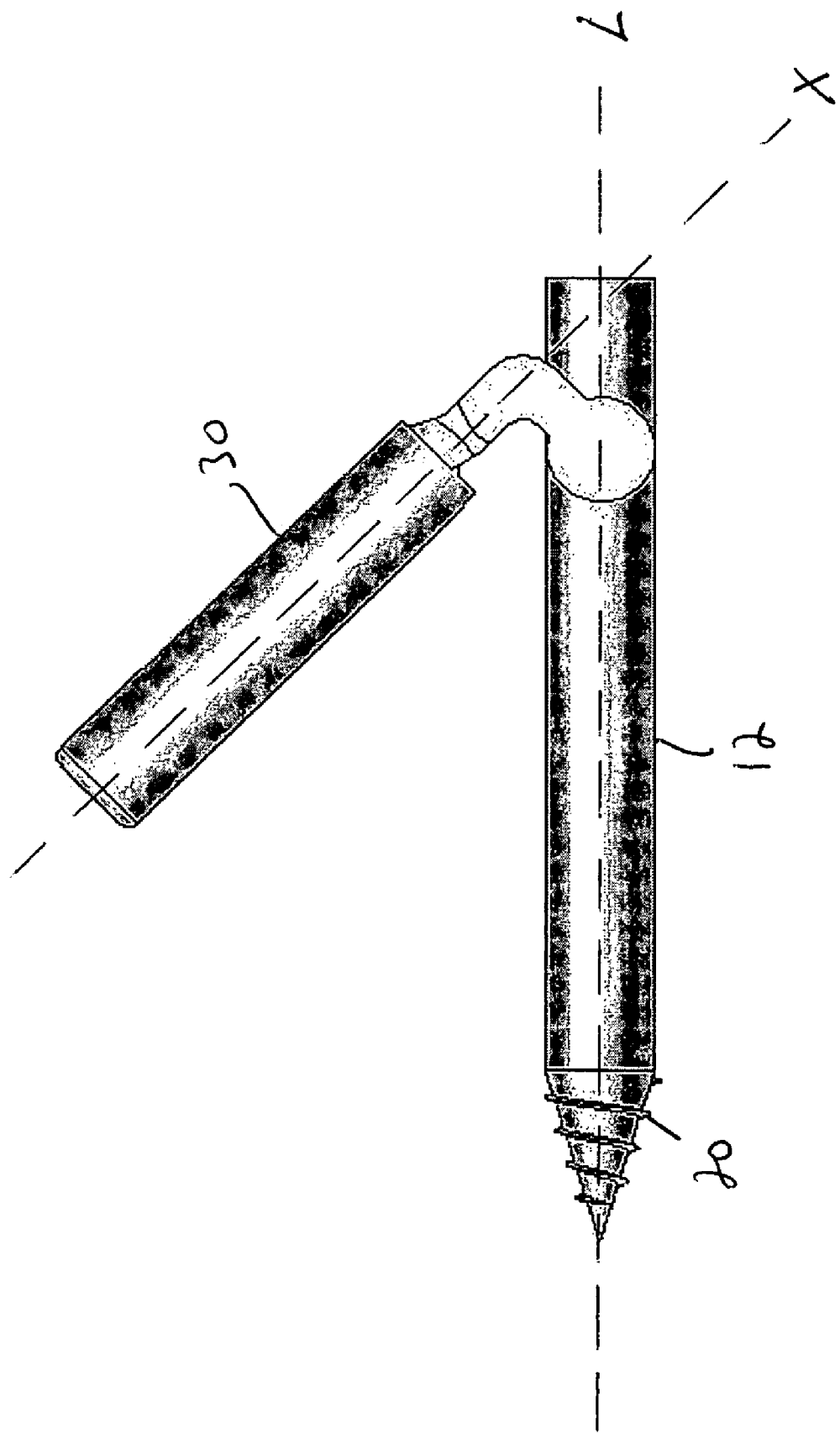
FIG. 9 is a side view of the brachytherapy applicator with bifurcated arm in an extended position.
Figure 10:
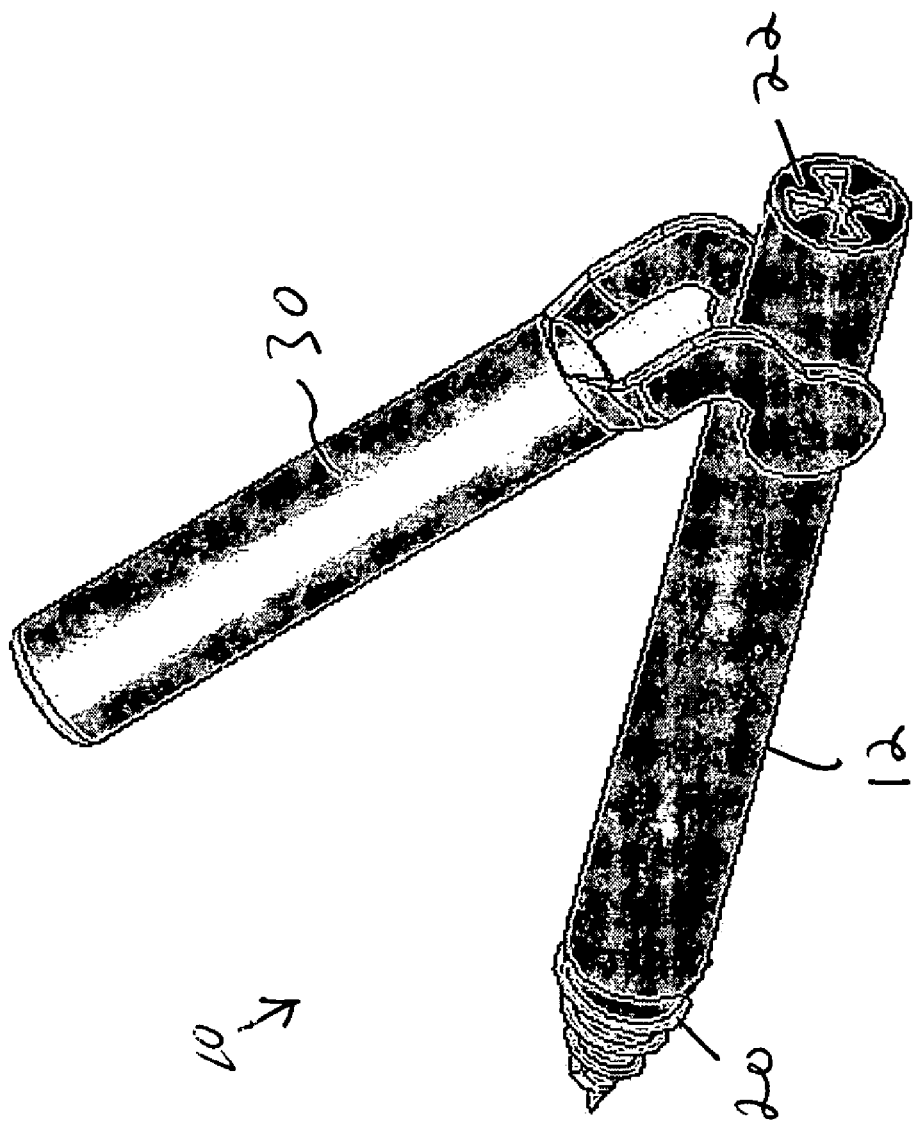
FIG. 10 is a perspective view of the applicator of FIG. 9.

FIGS. 7 and 8 illustrate bifurcation arm 30 in a parallel position with respect to body 12. Pivot 32 allows bifurcation arm 30 to pivot into position as shown in FIGS. 9 and 10. One skilled in the art will appreciate that the connection of the bifurcation arm 30 to body 12 shown in the FIGS. is exemplary, and that other types of articulation are contemplated. In addition, bifurcation arm 30 can include the feature of the body 12 as discussed above, particularly with respect to shaping, directing, and/or loading a radiation source. For example, the bifurcation arm can include an opening for admitting a radiation source, and the radiation source positioned therein can be shielded or arranged to deliver the most effective dose to target tissue while presenting the least damaging dose to adjacent healthy tissue.

The total radiation dose delivered from the applicator 10 will depend on a variety of factors and can be delivered at high rates (e.g., HDR), low rates (e.g., LDR), or ultra low rates (e.g., permanently implanted sources) with respect to a unit of time. In any case, applicator 10 can receive one or more sources of a photon (x-ray and/or gamma ray) emitting nuclide or mixed emitter (nuclide that emits photons and non-penetrating radiation such as beta particles). Also of utility would be manmade photon sources such as miniature x-ray sources.

When high radiation exposure rates around patient, while the source is deployed in the brachytherapy applicator, are not desirable, the radiation sources will preferentially emit photons of low photon energy. In one embodiment, the energy level is low enough to allow the delivery of HDR brachytherapy in an ordinary operating room (i.e., one with no or minimal additional shielding such as lead or concrete), a diagnostic radiology suite, and/or a suitably shielded or restricted location in a physician's office. For example, the radiation source could have a low enough energy that it could be used in a location approved for the use of diagnostic x-ray units or fluoroscopy units. The low photon energies in one embodiment are less than about 100 keV (kilo-electron volts). In another embodiment, the photon energy is less than 80 keV, and in yet another embodiment the photon energy is in the range of about 25 keV to 80 keV.

The low energy radiation source (e.g., <50 keV, <100 keV) can be one of the commercially available brachytherapy seeds, such as, for example seeds made with I-125, Pd-103, and Gd-153. Manmade photons from miniature x-ray sources could also provide a low energy radiation source.

Applicator 10 can be formed from a variety of materials capable of being sterilized (e.g., silicone, nylon, etc.), with preference for a metal such as stainless steel, titanium or other fairly rigid metal. One skilled in the art will appreciate that the chosen material can include both radiation lucent and radiation opaque materials. For example, radio-opaque materials such as, barium, tungsten, bismuth, tantalum, and tin could be coated on a surface of applicator 10 to shield sensitive tissue. As an alternative to coating, a radiation-blocking or absorbing shield (not shown) can be positioned between the radiation source and adjacent tissue to produce a desired isodose curve. A person having ordinary skill in the art will appreciate that other configurations may be employed to achieve the desired isodose curves and/or shielding of radiation sensitive tissue. The chosen materials can also have a variety of properties or features that aid in the procedure such as MRI compatibility.

In another aspect of the invention, applicator 10 can include markers to assist with locating and/or positioning the applicator within a patient. For example, fiducial markers, such as those disclosed in patent application Ser. No. 10/704,161, entitled "Tissue Positioning Systems and Methods for Use with Radiation Therapy," and incorporated herein by reference in its entirety, can be used to with applicator 10. In addition, radiation sensors can be used with or disposed on applicator 10 to assist with delivery of therapeutic radiation. Utility application Ser. No. 10/704,340, entitled, "Implantable Radiotherapy/Brachytherapy Radiation Detecting Apparatus and Method," and incorporated herein by reference in its entirety, discloses exemplary sensors.

A method for treating spinal metastases and other malignancies with applicator 10 generally begins with the step of surgically resecting a malignant tumor followed by implanting applicator 10 and providing a structural support. Structural support can be provided in a variety of ways known to one skilled in the art. For example, in a spinal procedure, a prosthetic disc or vertebra can be positioned to support and/or replace damaged spinal elements. Structural support can also be provided by way of a filling material implanted into a damaged vertebra. Applicator 10 can be implanted before, concurrently with, or after such stabilization procedures.

The placement of the applicator in relation to the bony structures of the spinal column would preferably be through open surgical or percutaneous access, in either a posterior (e.g., from the back) or an anterior (e.g., from the abdominal region) approach. It is contemplated that one or more of the brachytherapy applicators would be placed within a bony structure (e.g., vertebral body) to achieve as complete of radiation dosing coverage as possible to the bony structure. The applicator may be placed in the center of the bony structure (e.g., a single source system), bilaterally in a single plane, or bilaterally in multiple planes (e.g., inferior and superior planes).

Once the applicator is in position and secured to minimize movement during dosing, a therapeutic dose can be delivered to the target region. A radiation source, if not implanted with applicator 10, is then delivered to the applicator to provide a controlled dose of radiation to the surrounding tissue.

Both the applicator and/or the radiation source contained therein can be may be left in the bony structure and/or stabilizing element permanently or temporarily. For example, a radiation source can be placed within the applicator prior to implantation and sealed therein. The applicator is then surgically placed in relation to the target region in a secure manner (i.e., driven into a bony region to secure the applicator). The implanted applicator can then be left in position permanently to deliver the desired therapeutic dose. Alternatively, a second procedure could remove the radiation source (or part thereof) after a predetermined time.

In an alternative embodiment, the applicator could be implanted without the radiation source. For example, applicator 10 could be fixedly implanted in relation to the target region and hollow region 17 mated to a catheter via the opening at proximal end 16. The radiation source could then be implanted at the desired time through the catheter.

One of ordinary skill in the art will appreciate that the duration, delivery method (i.e., catheter), delivery timing (pre-, post-, or intra-operatively), dosage, and other treatment factors can vary depending on a physician's desired treatment regimen.

A person skilled in the art will appreciate that the brachytherapy system described therein can have virtually any configuration, and the embodiments illustrated and described herein are intended merely as exemplary embodiments and should not be construed to limit the present invention. Moreover, it will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. A brachytherapy applicator for delivering a therapeutic dose of radiation, comprising:
   an end piece;
   a substantially hollow tubular member extending longitudinally from the end piece and adapted to both affix the applicator to a patient and to deliver the therapeutic dose, the tubular member having a proximal end, a distal end defining a tip region and a length, the length of the tubular member having substantially solid outer walls defining an internal chamber for positioning one or more radiation sources therein, the one or more radiation sources adapted for forming a therapeutic radiation dosing profile disposed approximately centrally in relation to a treatment site, wherein the proximal end includes an opening to the internal chamber and a portion of the end piece seals the opening when the end piece is attached to the tubular member;
   a fixation element integrally formed with the solid outer walls on the tip region of the tubular member;
   radiation shielding disposed at one or more locations at least one of on and within the tubular member; and
   a catheter mated to the proximal end.

2. The applicator of claim 1, wherein the fixation element is a bone attachment element including a bone screw thread provided on a closed distal end of the tubular member.

3. The applicator of claim 1, wherein the outer surface of the tubular member includes a securement feature adapted to fix the applicator within a filling material after the filling material hardens.

4. The applicator of claim 3, wherein the securement feature includes one or more barbs.

5. The applicator of claim 3, wherein a depression in the tubular member provides the securement feature.

6. The applicator of claim 1, wherein the one or more radiation sources are configured to provide a radially symmetric radiation dose.

7. The applicator of claim 1, wherein the one or more radiation sources comprise a photon source providing less than about 100 keV.

8. The brachytherapy applicator of claim 7, wherein the one or more radiation sources provide energy in the range of about 25 keV to 80 keV.

9. The brachytherapy applicator of claim 1, wherein the one or more radiation sources comprise a miniature x-ray source.

10. The brachytherapy applicator of claim 1, therein the one or more radiation sources comprise a brachytherapy seed.

11. A brachytherapy applicator for delivering a therapeutic dose of radiation, comprising:
an end piece;
a substantially hollow tubular member extending longitudinally from the end piece and adapted to both affix the applicator to a patient and to deliver the therapeutic dose, the tubular member having a proximal end, a distal end defining a tip region and a length, the length of the tubular member having substantially solid outer walls defining an internal chamber for positioning one or more radiation sources therein, the one or more radiation sources adapted for forming a therapeutic radiation dosing profile disposed approximately centrally in relation to a treatment site;
a fixation element integrally formed with the solid outer walls on the tip region of the tubular member;
radiation shielding disposed at one or more locations at least one of on and within the tubular member; and
a bifurcated arm pivotally attached to the tubular member such that the arm can pivot relative to the tubular member.

12. The applicator of claim 11, wherein the bifurcated arm includes a radiation source configured to provide a therapeutic radiation dose.

13. The applicator of claim 11, wherein the one or more radiation sources provide a therapeutic dose of radiation of less than about 100 keV.

14. The applicator of claim 13, wherein the therapeutic dose is in the range of about 25 keV to 80 keV.

15. A method for treating proliferative tissue disorders by delivering a therapeutic dose of radiation in a load-bearing region, comprising:
providing an applicator comprising:
an end piece;
a substantially hollow tubular member extending longitudinally from the end piece and adapted to both affix the applicator to a patient and to deliver the therapeutic dose, the tubular member having a proximal end, a distal end defining a tip region and a length, the length of the tubular member having substantially solid outer walls defining an internal chamber for positioning one or more radiation sources therein, wherein the proximal end includes an opening to the internal chamber and a portion of the end piece seals the opening when the end piece is attached to the tubular member;
at least one fixation element integrally formed with the solid outer walls on the tip region of the tubular member;
radiation shielding disposed at one or more locations at least one of on and within the tubular member; and
a catheter mated to the proximal end;
implanting the applicator at a treatment site with the internal chamber of the tubular member centrally positioned relative to the treatment site;
positioning one or more radiation sources within the internal chamber, the one or more radiation sources forming a therapeutic radiation dosing profile disposed approximately centrally in relation to a treatment site; and
providing a therapeutic dose of radiation to the treatment site.

16. The method of claim 15, wherein the step of positioning the radiation source occurs before implanting the applicator.

17. The method of claim 15, wherein the therapeutic dose is less than about 100 keV.

18. The method of claim 15, wherein the step of positioning the radiation source occurs after the step of implanting the applicator.

19. The method of claim 15, wherein the applicator is implanted in bone.

20. The method of claim 19, wherein the applicator is implanted at least partially within a vertebral body.

21. The method of claim 15, wherein the applicator provides an asymmetric profile of therapeutic rays configured to protect a patient's spinal cord.

22. The applicator of claim 17, wherein the therapeutic dose is in the range of about 25 keV to 80 keV.

23. A method for treating proliferative tissue disorders by delivering a therapeutic dose of radiation, comprising:
providing a brachytherapy applicator for delivering a therapeutic dose of radiation comprising:
an end piece;
a substantially hollow tubular member extending longitudinally from the end piece and adapted to both affix the applicator to a patient and to deliver the therapeutic dose, the tubular member having a proximal end, a distal end defining a tip region and a length, the length of the tubular member having substantially solid outer walls defining an internal chamber for positioning one or more radiation sources therein, the one or more radiation sources adapted for forming a therapeutic radiation dosing profile disposed approximately centrally in relation to a treatment site;
a fixation element integrally formed with the solid outer walls on the tip region of the tubular member;
radiation shielding disposed at one or more locations at least one of on and within the tubular member; and
a bifurcated arm pivotally attached to the tubular member such that the arm can pivot relative to the tubular member;
implanting the applicator with the internal volume centrally positioned with regard to a treatment site;
positioning at least one radiation source within the internal chamber and bifurcated arm to provide a therapeutic dose of radiation at the treatment site; and
pivoting the bifurcated arm to a desired location relative to the tubular member.

24. The method of claim 23, wherein the therapeutic dose is less than about 100 keV.

* * * * *